(12) United States Patent
Wear et al.

(10) Patent No.: US 11,925,495 B2
(45) Date of Patent: Mar. 12, 2024

(54) METHODS AND SYSTEMS FOR A PIVOTING SOURCE WITH TRACKING DETECTOR FOR TRANSVERSE DUAL ENERGY ABSORPTIOMETRY

(71) Applicant: GE Precision Healthcare LLC, Milwaukee, WI (US)

(72) Inventors: James Wear, Madison, WI (US); Michael Buchholz, McFarland, WI (US)

(73) Assignee: GE PRECISION HEALTHCARE LLC, Milwaukee, WI (US)

( * ) Notice: Subject to any disclaimer, the term of this patent is extended or adjusted under 35 U.S.C. 154(b) by 211 days.

(21) Appl. No.: 16/733,159

(22) Filed: Jan. 2, 2020

(65) Prior Publication Data

US 2021/0204892 A1 Jul. 8, 2021

(51) Int. Cl.
*A61B 6/00* (2006.01)
*A61B 6/03* (2006.01)

(52) U.S. Cl.
CPC .......... *A61B 6/4452* (2013.01); *A61B 6/032* (2013.01); *A61B 6/482* (2013.01)

(58) Field of Classification Search
CPC .............................. A61B 6/4452; A61B 6/482
See application file for complete search history.

(56) References Cited

U.S. PATENT DOCUMENTS

| 5,418,832 | A | * | 5/1995 | Barnes | G21K 1/10 378/146 |
|---|---|---|---|---|---|
| 5,715,820 | A | * | 2/1998 | Stein | A61B 6/482 378/146 |
| 5,729,584 | A | * | 3/1998 | Moorman | G01T 1/20182 378/146 |
| 5,838,765 | A | * | 11/1998 | Gershman | A61B 6/482 378/196 |
| RE36,162 | E | * | 3/1999 | Bisek | A61B 6/5241 378/146 |
| 6,217,214 | B1 | * | 4/2001 | Cabral | A61B 6/505 378/208 |
| 7,203,274 | B2 | * | 4/2007 | Charles, Jr. | A61B 6/482 378/54 |
| 8,165,266 | B2 | | 4/2012 | Wear et al. | |
| 2004/0202289 | A1 | * | 10/2004 | Settergren | A61B 6/405 378/209 |
| 2014/0185746 | A1 | * | 7/2014 | Baturin | G21K 1/06 378/36 |

* cited by examiner

*Primary Examiner* — Christine S. Kim
(74) *Attorney, Agent, or Firm* — McCoy Russell LLP (57) ABSTRACT

Various systems are provided for an X-ray system. In one example, an X-ray system comprises an X-ray source positioned opposite to and facing a first side of a table and an X-ray detector positioned directly opposite to and facing a second side of the table, wherein the second side is opposite the first side, wherein the X-ray source is a dual-energy X-ray source configured to scan in a raster pattern. In one example, an object is positioned on the first side of the table.

26 Claims, 6 Drawing Sheets

METHODS AND SYSTEMS FOR A PIVOTING SOURCE WITH TRACKING DETECTOR FOR TRANSVERSE DUAL ENERGY ABSORPTIOMETRY

TECHNICAL FIELD

Embodiments of the subject matter disclosed herein relate to medical imaging, and more particularly, X-ray imaging

DISCUSSION OF ART

Dual energy x-ray absorptiometry (DXA) relies on energy measurements of low- and high-energy x-rays with minimal contamination of the primary x-ray beam from scattered radiation. Differences in x-ray attenuation between low- and high-energy x-rays permit quantitative estimate of two distinct elemental components of the object of interest. In humans this is commonly used to measure bone mineral density. One approach is to scan the patient with a narrow fan-beam of x-rays, which reduces scatter. Scans are commonly constructed of transverse sweeps in a raster pattern across the region of interest. Image analysis reconstructs a planar image of the region of interest and calculates accurate measurements of area and bone mineral density. Typical regions of interest are the lumbar spine and proximal femur for osteoporosis diagnosis and monitoring. Alternate sites in peripheral regions of the body may also be measured. Another application of DXA measurements is to scan the entire body and measure its lean and fat mass.

BRIEF DESCRIPTION

In one embodiment, an X-ray system comprises an X-ray source positioned above a first side of a table and an X-ray detector positioned directly below a second side of the table, the second side opposite the first side, wherein a patient is positioned on the first side, wherein the X-ray source is a dual-energy X-ray source configured to scan in a raster pattern.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Figure 1:
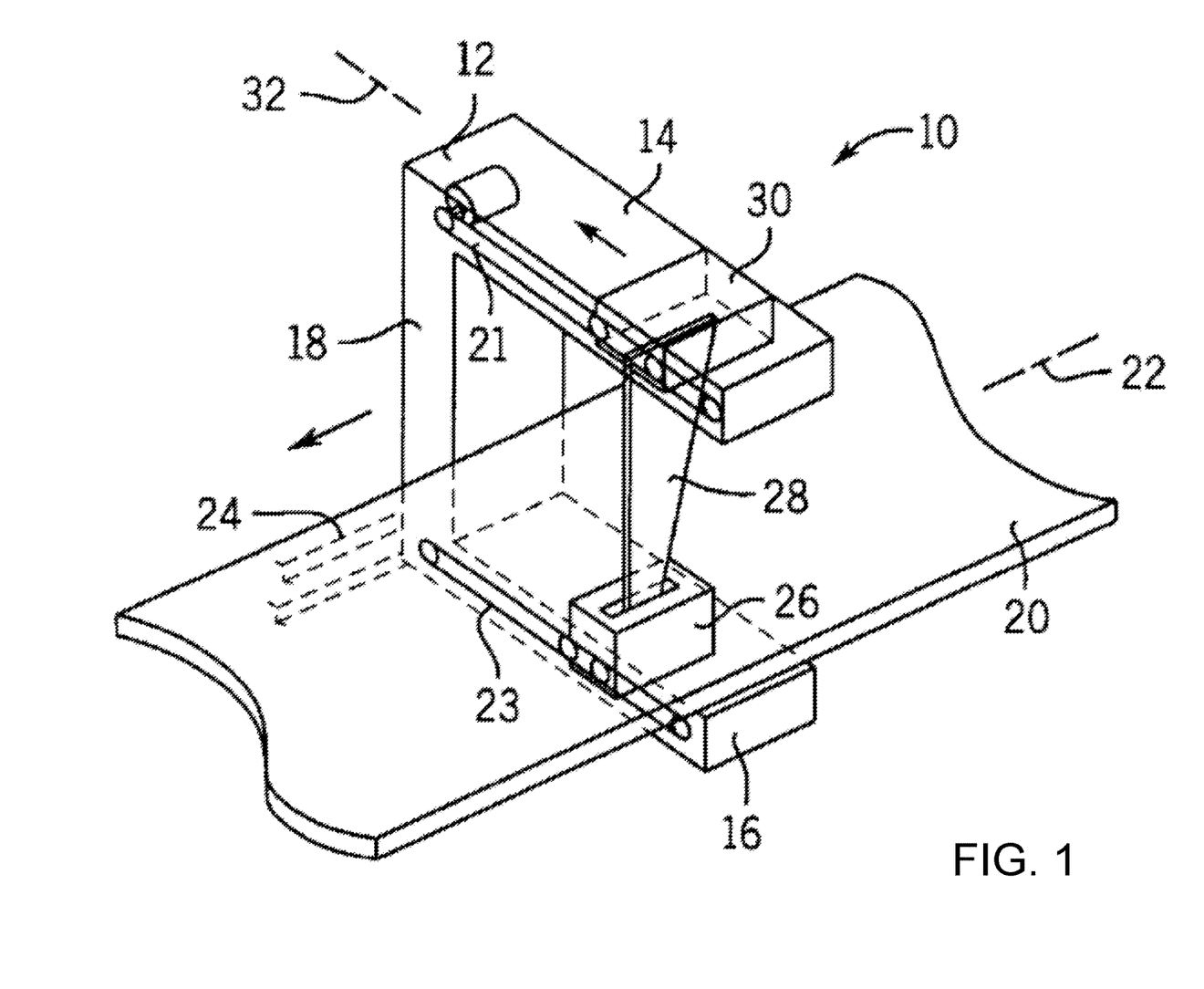
FIG. 1 shows a perspective view of a transverse scanning densitometer.
Figure 2:
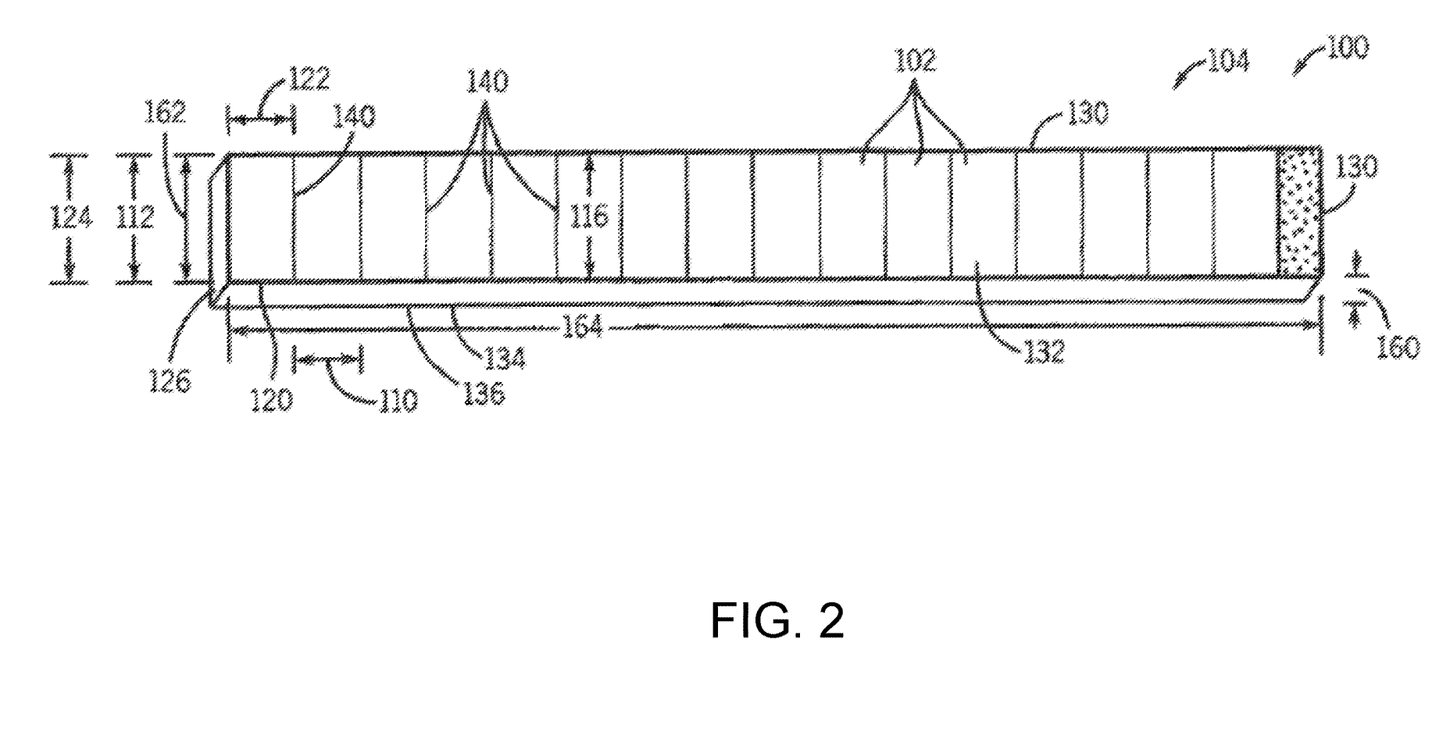
FIG. 2 shows a detector that may be used with the imaging system of FIG. 1.

The following description relates to embodiments of an X-ray system. In one example, the X-ray system of the present disclosure may be configured to decrease transverse scanning times. Furthermore, the X-ray system of the present disclosure may decrease radiation entrance doses to the patient. FIG. 1 diagrammatically illustrates a medical imaging system. FIG. 2 illustrates an example of an X-ray detector. The previous example comprises an X-ray source arranged directly below a first side of a table on which a patient or object to be scanned is arranged. A detector may be arranged opposite a second side of the table, wherein the patient or object is in direct contact with the second side.

Figure 3:
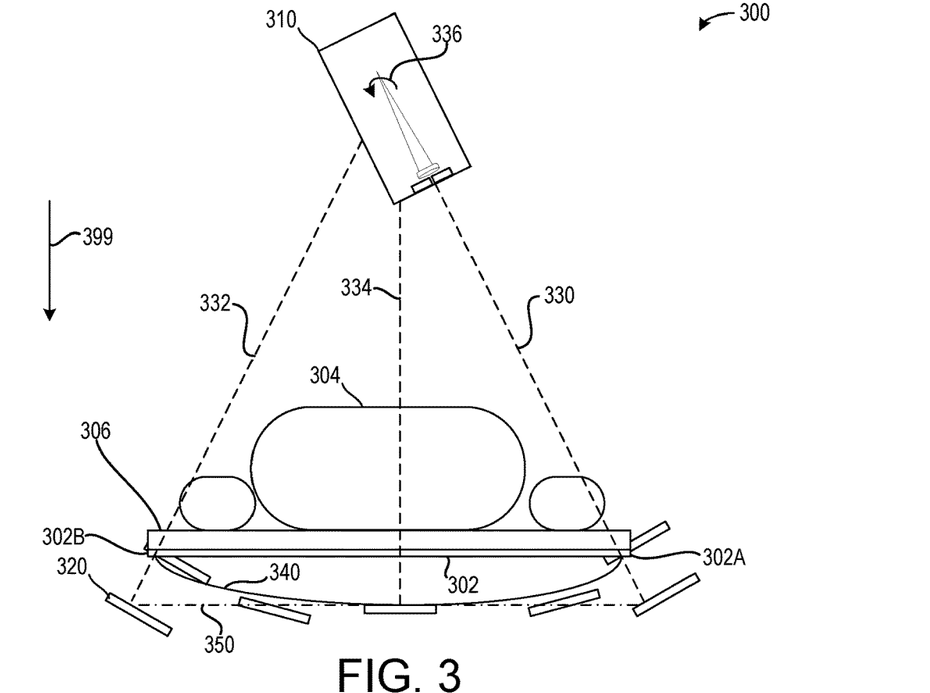
FIG. 3 illustrates a first embodiment of an X-ray imaging system of the present disclosure.
Figure 4:
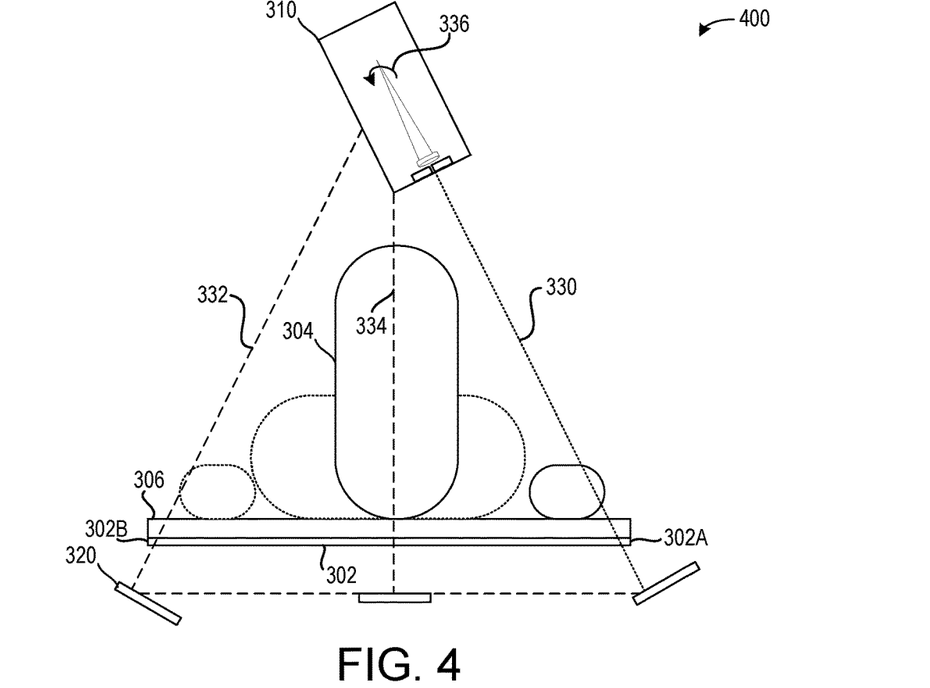
FIG. 4 illustrates a second embodiment of an X-ray imaging system of the present disclosure.
Figure 5:
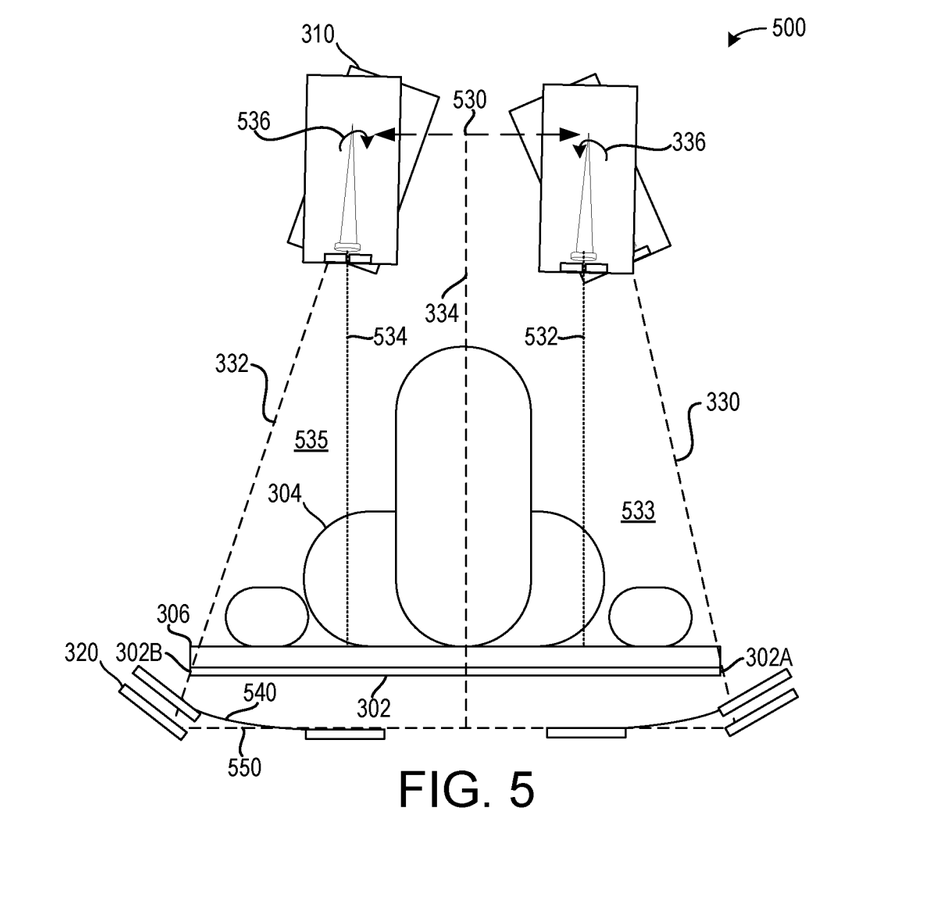
FIG. 5 illustrates a third embodiment of an X-ray imaging system of the present disclosure.
Figure 6:
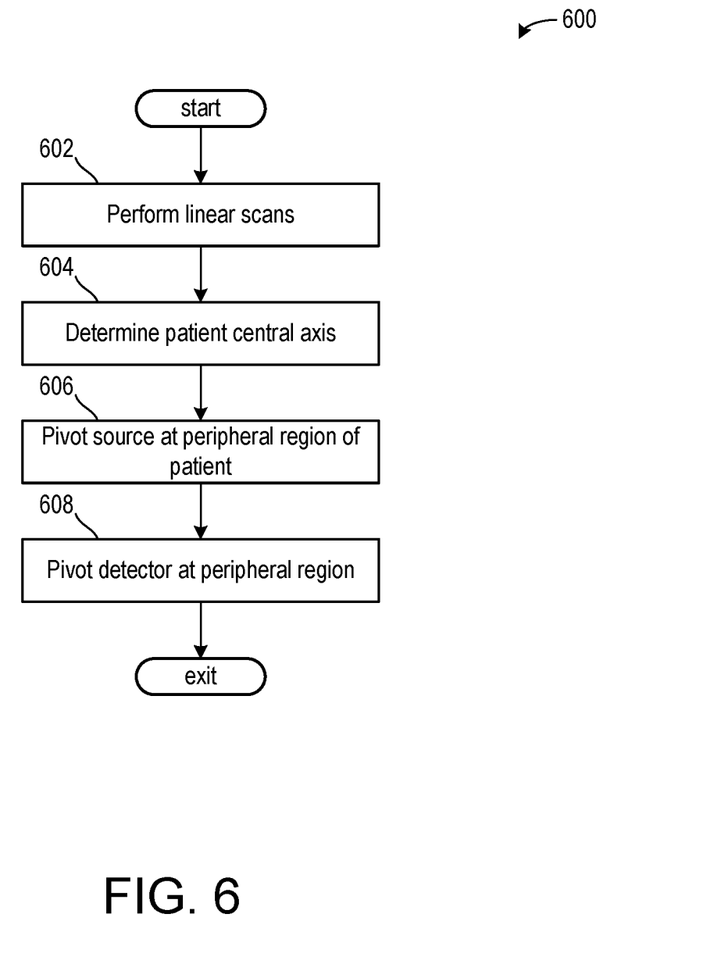
FIG. 6 illustrates a method for operating the X-ray imaging system.

FIGS. 3, 4, 5 and 7A, illustrate various embodiments of an X-ray system of the present disclosure. The embodiments illustrate a reverse positioning of the X-ray source and the X-ray detector relative to the previous examples. As such, in the examples of FIGS. 3, 4, 5 and 7A, the X-ray detector is arranged below the first side of the table and the X-ray source is arranged above the second side of the table. An example method of operating the embodiment illustrated in FIG. 5 is illustrated in FIG. 6.

By inverting the arrangement of the X-ray detector and the X-ray source to the orientations illustrated in FIGS. 3-5, a fan-beam length at an object is increased relative to previous examples. As such, a scan duration may decrease. Additionally, a skin entrance dose of radiation from the X-ray source may decrease due to the increased distance between the X-ray source and the object (e.g., the patient). In one example, the reversed arrangement may allow faster transverse scanning relative to the previous examples. The elongated fan-beam may result in fewer transverse scan sweeps to scan the entire patient. This arrangement may present certain mechanical challenges. In one example, the X-ray source is relatively heavy and actuation of the X-ray source to achieve faster scan times is difficult. The X-ray source of the present disclosure may be pivoted to achieve the faster scan times described above.

FIGS. 3-5, and 7A-7B show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

Referring now to FIG. 1, a densitometer 10 includes a support arm 12 having vertically opposed horizontal arms 14 and 16 separated by vertical bar 18. Between the arms 14 and 16 is a horizontal planar patient support table 20 extending along a longitudinal axis 22. A belt drive system 24 of a type well known in the art allows motion of the arm 12 longitudinally along axis 22 for the length of the table 20.

Positioned within the lower arm 16 is an x-ray source 26 providing a collimated fan beam 28 of x-rays directed upward through the table 20 to the arm 14 where it may be received by a linear detector 30. The fan beam 28 is oriented so that its narrowest extent is along the transverse axis and its widest extent along the longitudinal axis 22. The table 20 is generally radiolucent so as to provide a support surface without significantly affecting the attenuation of the fan beam 28.

The x-ray source 26 and linear detector 30 may be moved transversely along transverse axis 32 as encased in arms 16 and 14, respectively, so as to provide transverse scans of the patient on the table 20. Motion of the x-ray source 26 and detector 30 is synchronized by belt drive actuation mechanisms 21 held within arms 16 and 14 as will be well understood to those of ordinary skill in the art.

FIG. 2 is an illustration of an exemplary detector 100 including a plurality of detector elements 102 arranged as a linear array that may be used with the imaging system 10 shown in FIG. 1. In one embodiment, the plurality of detector elements 102 are formed as a monolithic structure on a single ceramic substrate. Optionally, the plurality of detector elements 102 are fabricated individually and then assembled together to form the detector 100. In the exemplary embodiment, the detector 100 includes a plurality of detector elements 102, illustrated as sixteen cadmium tellurium (CdTe) detector elements 102 that are oriented to form the linear array 104. An alternate embodiment of the linear array 104 utilizes yttrium-doped lutetium oxyorthosilicate (LYSO) scintillator coupled to silicon photomultiplier diodes.

Referring again to FIG. 2, in the exemplary embodiment, at least some of the detector elements 102 have a width 110 that is approximately 3 millimeters and a length 112 that is approximately 5 millimeters. It should be appreciated that the width 110 and the length 112 of the detector elements 102 is exemplary and that other widths and lengths may be selected based on the imaging application. In one example, the embodiments of FIGS. 3-5 illustrate example of an x-ray source positioned above a table on which a patient is arranged and an x-ray source positioned below the table. The x-ray source may be a poly-energetic (e.g., dual energy or higher) x-ray source configured to scan in a raster pattern. Raster scanning a heavy x-ray source presents mechanical challenges, which have been at least partially solved by the inventors herein. By pivoting the source, inverse scanning geometry for transverse scanning DXA is enabled. More specifically, transverse scanning which is achieved through pivoting the source reduces the desire to translate a heavy x-ray source at a relatively high speed. Smaller and lighter x-ray detectors are more easily moved at higher speeds while maintaining alignment to the fanbeam. Combining central transverse scanning with reduced-range pivot at the scan window periphery maintains image reconstruction methods of central DXA, which encompass a majority of DXA scans presently executed. The configuration may allow the heavy source (e.g., the x-ray source) to be moved via a low-powered motor due to the angular velocity achieved. As such, a packaging size of the x-ray source may be reduced and an efficiency increased.

Turning now to FIG. 3, it shows a first embodiment 300 of an X-ray device of the present disclosure. The first embodiment 300 comprises a table 302, on which an object 304 may be positioned. Herein, the object 304 is a patient 304 and the X-ray device is configured to capture a medical image of the patient 304. A pad 306 may be arranged between the patient 304 and the table 302. The pad 306 may comprise a material that is more compressible than a material of the tabletop.

The pad 306 is arranged on a first side of the table 302, the first side proximal to the patient 304. The table 302 further comprises a second side, opposite the first side, free of a pad or other devices, the second side proximal to an X-ray detector 320. In one example, the second side is exposed to an ambient atmosphere.

An X-ray source 310 is arranged distal to the table 302. In one example, the X-ray source 310 is arranged vertically above the table relative to a direction of gravity 399. The X-ray detector 320 is arranged below the table 302. As such, radiation from the X-ray source 310 may penetrate the patient 304, then the pad 306, then the table 302, before reaching the X-ray detector 320. In this way, the first embodiment 300 may differ from the previous examples in at least that the X-ray source 310 and the X-ray detector 320 are inverted relative to the X-ray source and the X-ray detector of the previous example illustrated in FIG. 2. As mentioned above, by increasing a distance between the X-ray source and the table 302, a skin dose and scan times may be reduced.

More specifically, the X-ray source 310 faces the first side of the table 302 and the X-ray detector 320 faces the second side of the table 302. In one example, the X-ray detector 320 is closer to the table 302 than the X-ray source 310. A patient is arranged on the first side of the table 302. In one example, the first side of the table 302 faces a direction opposite gravity.

The X-ray source 310 may provide an X-ray beam from a first side region 330 to a second side region 332. As illustrated, the side regions correspond to edges of the table 302. In one example, the X-ray source 310 may direct X-rays from the first side region 330 to the second side region 332 and to a plurality of positions therebetween, such as a central region 334. In one example, a pivot of the X-ray source 310, illustrated by arrow 336, may result in a transverse sweep of the patient 304.

The X-ray source 310 may pivot to sweep a fan-beam transversely across the patient 304 from the first side region 330 to the second side region 332. The X-ray detector 320 positioned below the table 302 may receive the fan-beam post-attenuation. The X-ray detector 320 may translate and/or rotate to track the fan-beam as it moves transversely. The X-ray detector 320 may sample X-ray intensity along a path of motion and/or a travel path.

The first side region 330 may correspond to a first edge 302A of the table 302 and the second side region 332 may correspond to a second edge 302B of the table 302. In this way, a pivot range of the X-ray source 310 may be from the first edge 302A to the second edge 302B.

The X-ray detector 320 may comprise two separate travel paths. A first travel path 340, illustrated via a solid line, may represent a fixed source-to-image (SID) distance, which may permit constant velocity motion while receiving a constant nominal beam intensity. As illustrated, the first travel path 340 may comprise an arc shape such that the SID distance is fixed and does not change along an entire distance of the first travel path 340. In one example, the SID distance is 75 cm±5 cm. However, the SID distance may be increased or decreased without departing from the scope of the present disclosure.

In one example, additionally or alternatively, a second travel path 350 may comprise where the X-ray detector 320 travels in a straight line parallel to the table 302. The second travel path 350 is illustrated via a dash-dot line. As such, the X-ray detector 320 may travel transversely in order to maintain alignment with the fan-beam. In one example, the X-ray detector 320 moves in lock-step with the X-ray source 310. In one example, a shortest distance between the X-ray detector 320 and the X-ray source 310 is at the central region 334, and a greatest distance at the first side region 330 and the second side region 332. In one example, the shortest distance is 75 cm±5 cm and the greater distance is 85±5 cm.

Due to a varying SID distance during the second travel path 350, beam intensity corrections may be calculated. In one example, the calculations may be dual-energy X-ray absorptiometry (DXA) calculations. These calculations may be calculable via the inverse square distance law and feedback regarding a precise SID value at each detector position.

Turning now to FIG. 4, it shows an embodiment 400 of the X-ray source 310 and the X-ray detector 320. As such, components previously introduced may be similarly numbered in this figure and in subsequent figures. In the second embodiment, the patient 304 is arranged in on their side for a lateral vertebral assessment (LVA). In such an example, the detector 320 may be positioned to provide a greater SID distance (e.g., 75 cm±5 cm, 80 cm±5 cm, 85 cm±5 cm, 90 cm±5 cm, 95 cm±5 cm, etc.). In one example, the X-ray detector 320 may follow a straight line path, such as travel path 410 as illustrated. Additionally or alternatively, the X-ray detector may follow an arc path to maintain a desired SID distance. Furthermore, a wider fan-beam at the patient may be achieved, which may result in faster total body (TB) scans relative to previous examples which do not comprise a pivoting x-ray source and x-ray detector and/or the configuration of the x-ray source above the patient, further away from the table relative to the x-ray detector.

Turning now to FIG. 5, it shows an embodiment 500 of the X-ray system comprising the X-ray source 310 and the X-ray detector 320. In the embodiment 500, the X-ray source 310 may pivot, as in the previous embodiments 300 and 400, wherein the X-ray source 310 may be further configured to actuate along a linear track 530. The X-ray source 310 may perform a plurality of transverse sweeps along the linear track 530 without performing a pivot. That is to say, an actuator is configured to move the X-ray source 310 along the linear track 530 in a direction parallel to the table 302 such that the fan-beam is normal to the first surface of the table 302.

In one example of the embodiment 500, the X-ray source 310 is pivoted to direct fan-beams from a first linear track edge 532 to the first side region 330 and/or the first edge 302A. Herein, an area between the first linear track edge 532 and the first side region 330 is a first peripheral area 533. The X-ray source 310 may be pivoted in a counterclockwise direction at the first peripheral area 533 to sweep from the first linear track edge 532 to the first side region 330. Upon returning from the first side region 330 to the first linear track edge 532, the X-ray source 310 may be pivoted in the clockwise direction.

Additionally, the X-ray source 310 may be pivoted at a second linear track edge 534 to sweep a second peripheral area 535 arranged between the second linear track edge 534 to the second outer region 332. The X-ray source 310 may be pivoted in a clockwise direction, illustrated by arrow 563, to direct fan-beams from the second linear track edge 534 to the second outer region 332. Upon returning from the second outer region 332 to the second linear track edge 534, the X-ray source 310 may pivot in the counterclockwise direction. As such, pre-existing algorithms may be used during linear sweeps along the linear track 530. However, for sweeps along the first and second peripheral areas 533 and 535 where the X-ray source 310 pivots, new algorithms may be used as previously described.

By incorporating the linear track 530, an area in which the X-ray source pivots may be reduced relative to the examples of FIGS. 3 and 4. As such, scan times may be reduced due to linear sweeps being executed more quickly than pivot sweeps.

An actuator of the X-ray source 310 may comprise a camshaft or other mechanism configured to pivot the X-ray source. A similar actuator may be used to pivot the X-ray detector 320. The X-ray detector 320 may be tracked along an arc path 540 or a linear path 550. In the example of the embodiment 500, by actuating the X-ray source 310 in a straight line, the X-ray detector 320 may be pivoted only closer to edges of the table 302. By doing this, the X-ray detector 320 path may comprise less of an arc relative to the embodiments 300 and 400, allowing use of pre-existing algorithms. Furthermore, the table 302 may be narrowed.

In one example, the embodiment 500 allows a synchronous X-ray source 310 and X-ray detector 320 transverse scanning method for central regions at and between the first edge 532 and the second edge 534. Additionally, the X-ray source 310 and the X-ray detector 320 may pivot from the first and second linear track edges 532, 534 to the first side region 330 and the second side region 332, respectively. A normal incidence may be maintained as the X-ray source 310 and the X-ray detector 320 are pivoted. In one example, actuators used to pivot the X-ray source 310 and the X-ray detector 320 may be operated independently, wherein the operation of the actuator of the X-ray detector 320 may be adjusted based on an angle of incidence at the X-ray detector 320.

In one exemplary embodiment of the embodiment 500, scan times may be reduced by separating the linear sweeps and the pivot sweeps. That is to say, for certain patient sizes or scanning areas of interest, pivot sweeps at a periphery may be omitted and only linear sweeps may be performed. However, in other scan types, linear sweeps and pivot sweeps may be combined such that each linear sweep is followed by a pivot sweep. Thus, scanning patterns may be adjusted for different scan types.

In one example, the central axis may be estimated by performing fast, limited range transverse scout sweeps across at least 2 longitudinal positions along the body. The optimal sites would be the head and knees but the important quality it that 2 sweep positions are located at the longitudinal extremes of the patient. Detector's transverse and longitudinal position are registered to the scanner's reference system. On each sweep the lateral edges of the bone ($x_{ij}$, $z_i$) are determined by applying a threshold to the ratio of logged low energy intensity to logged high energy intensity. The x-coordinates required for calculating the patient central axis are $x_{ic}=(x_{i2}-x_{i1})/2$. The formula for the x-coordinate for central axis on sweep j is $x_{jc}=(x_{c2}-x_{c1})/(z_2-z_1)*(z_j-z_0)+x_{0c}$, where index 0 refers to the initial sweep of the full scan. Note that additional scout sweeps could be used to allow a linear regression fit to determine the central axis, preferentially at the pelvis and/or thoracic spine. The x-ray source tube current may be extremely low and scout scan speed relatively fast to minimize patient dose, since the beam attenuation change is large at the bone edges and easily detected.

In this way, FIGS. 3 through 5 illustrate an example of an X-ray imaging system comprising an inverse source geometry relative to previous examples, wherein the X-ray source is arranged above the patient and the X-ray detector is arranged below the patient. As such, a fan-beam provided by the X-ray source may penetrate the patient prior to penetrating the pad and the table. The fan-beam may be intercepted by the X-ray detector following passing through the table. The inverse source geometry may decrease scanning times. For example, DXA scan durations may be reduced by about 50%. In an example of total body scans, the reduction in total scan time along with the increased fan-beam length may decrease a skin entrance dose. In one example, the skin entrance dose may correspond to an amount of radiation that enters the patient. Furthermore, by combining the translation and peripheral-region pivots, a table width may be reduced compared to an arrangement where only pivots are used.

Turning now to FIG. 6, it shows a method 600 for operating an X-ray source and detector. Instructions for carrying out method 600 and the rest of the methods included herein may be executed by a controller based on instructions stored on a memory of the controller and in conjunction with signals received from sensors of the medical imaging system, such as the X-ray source and X-ray detector described above with reference to FIGS. 3-5. The controller may employ actuators of the medical imaging system to adjust X-ray source and X-ray detector operation, according to the methods described below.

In one example, the method 600 is described with respect to the embodiment 500 of FIG. 5. As such, the X-ray source may be configured to actuate linearly along a central region and then pivot at a periphery region.

The method 600 begins at 602, which comprises performing linear sweeps. An X-ray source actuator may move the X-ray source in a linear direction, parallel to a surface of a table, wherein the X-ray source sweeps between a first and second edges of the linear track.

The method 600 proceeds to 604, which comprises determining a central axis of the patient. In one example, this may include performing a plurality of linear sweeps, wherein desired sites captured via the linear sweeps may be analyzed by the controller to approximate a central axis of the patient.

The method 600 proceeds to 606, which comprises pivoting the X-ray source at a peripheral region of the patient. In one example, the peripheral region extends beyond the first and second edges of the linear path, wherein the peripheral region flanks the central region. In one example, the peripheral region extends from a first table edge to the first edge and from a second table edge to the second edge.

The method 600 proceeds to 608, which comprises pivoting the detector at the peripheral regions. In one example, the pivoting is based on a position of the X-ray source such that normal incidence is maintained between the X-ray source and the X-ray detector.

In one example of the method 600, determination of the patient central axis at 604 may be omitted. Furthermore, linear sweeps and pivot sweeps may be combined into a single continuous motion such that the X-ray source sweeps the central region and the peripheral regions along a single sweep. Thus, in one example, the X-ray source may begin from at the central region, wherein the X-ray source is actuated linearly from the central region to the first edge without pivoting. Upon reaching the first linear track edge, the X-ray source may pivot counterclockwise from the first edge to the first table edge. The X-ray detector may be similarly pivoted to maintain normal incidence. Upon sweeping up to the first table edge, the X-ray source, and X-ray detector, may be pivoted clockwise to return to the first linear track edge and linearly travel to the second linear track edge. Following reaching the second linear track edge, the X-ray source and the X-ray detector may be pivoted clockwise form the second edge to the second table edge. The X-ray source and the X-ray detector may be pivoted counterclockwise back to the second linear track edge. In such an example of the method 600, the table may be narrowed and an arc of the travel path may be less curved.

Figure 7A:
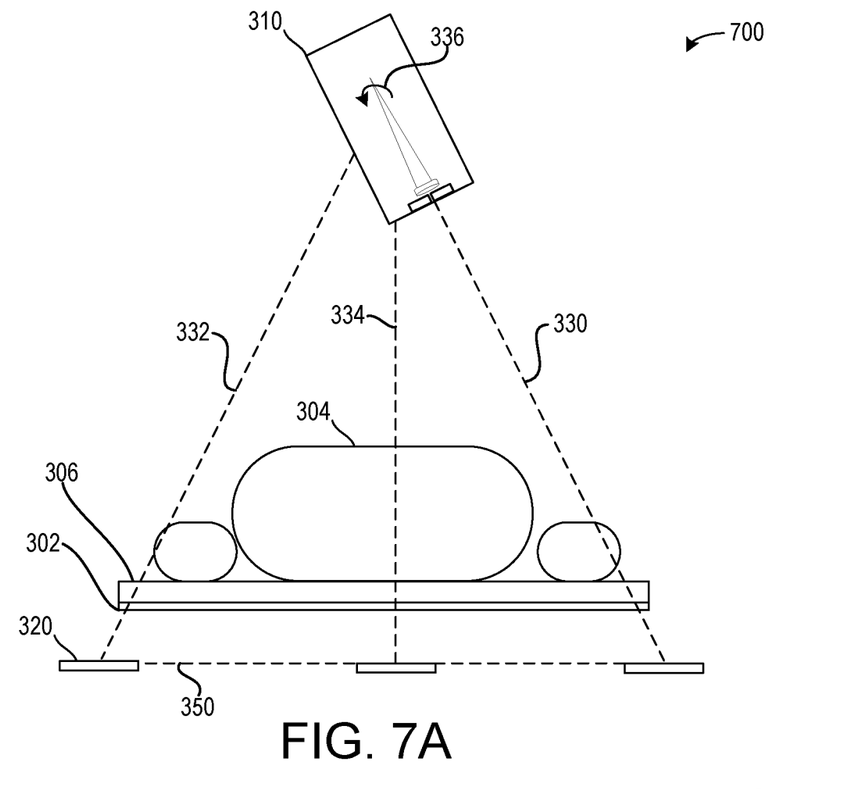
FIG. 7A illustrates an embodiment of the X-ray imaging system wherein the detector moves along a linear path.

Turning now to FIG. 7A, it shows an embodiment 700 of an X-ray device substantially similar to the embodiment 300 of FIG. 3. The embodiment 700 may differ in that the X-ray detector 320 may not pivot. As such, the X-ray detector 320 remains parallel to the table 302 during all its movements along the travel path 350. In the embodiment 700, the fan-beam may not be normal to the X-ray detector 320 outside of the central axis 334. As such, the X-ray detector may comprise a blocker arranged adjacent to an aperture of the X-ray detector 320. As will be described in below with respect to FIG. 7B, the blocker is configured to accommodate different angles of incidence of x-ray beam due to the pivoting source, while maintaining a constant illuminated area on the sensor and reducing the impact of scattered radiation Turning now to FIG. 7B, it shows an aperture 750 of the X-ray detector 320 in greater detail. Additionally or alternatively, the example of FIG. 7B may be a non-limiting example of detector 100 of FIG. 2. The aperture 750 comprises an opening 752 through which a fan-beam may travel following travel through the patient 304 and the table 302. The opening 752 may be shaped through two blockers, a first blocker 754 and a second blocker 756. In one example, the x-ray sensor 758 comprises cadmium telluride CdTe). The blocker 754 is comprised of less expensive, easily machined high density material. The blocker 756 may comprise a higher density material, such as tungsten (W), which may be configured to reduce a shadowed area in closest proximity to the detector sensor. In one example, the shadowed area may move across the x-ray sensor 758 and under the blocker 756. The shadowed area may comprise a width of up to 0.5 mm. A brass plate 754 may be configured to decrease scanner scatter. In one example, the x-ray sensor 758 may comprise a 6 mm width±2 mm. The blocker 756 may comprise a thickness of 1 mm±0.5 mm. The aperture 752 may comprise a width of 5 mm±1 mm at the surface of the x-ray sensor 758 The brass plate 754 may comprise a thickness of 6 mm±1 mm. The aperture in the blocker 754 consists of a narrowing throat from incoming x-ray beam face toward the sensor blocker 756 and x-ray sensor 758. The aperture 752 has sides that become normal to the sensor blocker 756 a few millimeters above the sensor blocker 756.

Figure 7B:
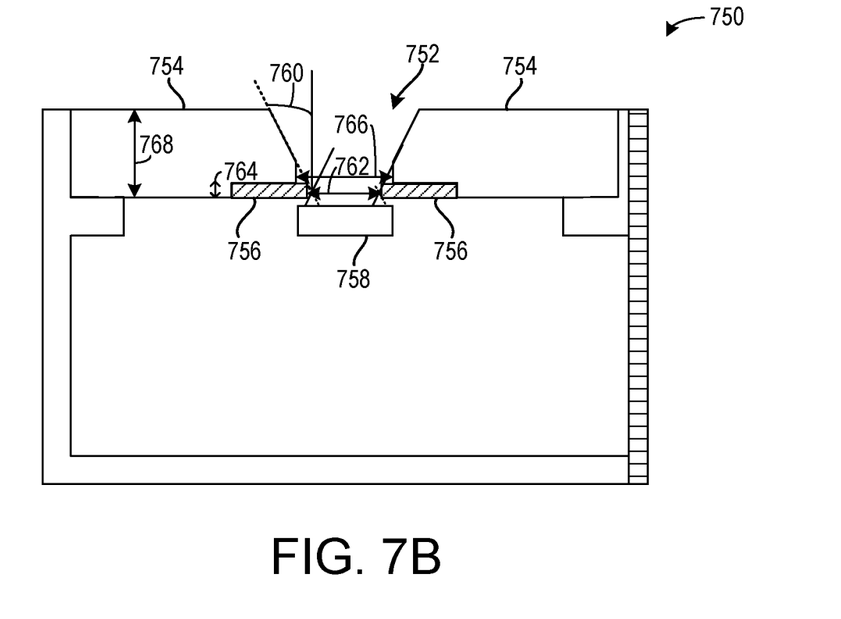
FIG. 7B illustrates an embodiment of a blocker integrated into the detector to adjust an angle of incidence.

This right-angled pocket serves to better capture x-rays scattered off the blocker face 754 near the x-ray sensor 758.

In one example, a shadow of up to 0.5 mm moves across the x-ray sensor 758, which is a CdTe sensor, and under the blocker 756, which comprises tungsten (W). To decrease scanner scatter and to enhance the fan beam to an effective fan beam via optimizing an aperture throat angle 760. A 5 mm wide and 6 mm thick brass plate with an open throat for increased pivot at the table periphery is included. More specifically, the second blocker 756 comprises a sensor aperture 762 of 5 mm and a thickness 764 of 1 mm. The first blocker 754 comprises a throat aperture 766 of 6 mm and a thickness 768 of 6 mm. The aperture throat angle 760 may be determined based on a table width and twice a source to image distance (SID). As such, the brass plate 754 may comprise a bevel based on the determined aperture throat angle to accommodate the pivoting of the x-ray source.

In this way, an X-ray system may comprise an X-ray source facing a first side of a table on which an object is positioned and an X-ray detector facing a second side of the table opposite the first side. The technical effect of inverting the position of the X-ray source and the X-ray detector is to decrease scan times and decrease a radiation dose. By doing this, X-ray imaging may be more efficient.

An embodiment of an X-ray system, comprises an X-ray source facing a first side of a table and an X-ray detector facing a second side of the table, the second side opposite the first side, wherein an object to be scanned is positioned on the first side, wherein the X-ray source is a dual-energy X-ray source configured to scan in a raster pattern.

A first example of the X-ray system, further comprises where the X-ray source is configured to actuate linearly along a first region and pivot along a second region.

A second example of the X-ray system, optionally including the first example, further comprises where the first region is a central region, and wherein the second region is a peripheral region arranged between edges of the central region and edges of the table.

A third example of the X-ray system, optionally including one or more of previous examples, further includes where the X-ray detector is configured to actuate linearly along the first region and pivot along the second region to maintain a normal angle of incidence between a fan-beam of the X-ray source and the X-ray detector.

A fourth example of the X-ray system, optionally including one or more of the previous examples, further includes where the X-ray detector is configured to travel along an arc-shaped travel path, wherein the arc-shaped travel path maintains a fixed contact source-to-image distance.

A fifth example of the X-ray system, optionally including one or more of the previous examples, further includes where the X-ray detector is configured to travel along a straight line path parallel to the second side of the table.

A sixth example of the X-ray system, optionally including one or more of the previous examples, further includes where the X-ray detector is configured to actuate linearly along the first region, and wherein the X-ray detector is configured to pivot along the second region adjacent to an edge of the table, wherein the X-ray detector is configured to move in lock step with the X-ray source.

An embodiment of an X-ray imaging device, comprising a table comprising a first side on which a patient may be positioned and a second side, opposite the first side, facing away from the patient, an X-ray source positioned closer to the first side than the second side and an X-ray detector positioned closer to the second side than the first side, wherein the X-ray source and the X-ray detector are configured to follow linear paths parallel to the table and pivot at peripheral regions corresponding to edges of the table, and a controller with computer-readable instructions stored on non-transitory memory thereof that when executed enable the controller to actuate the X-ray source and X-ray detector along a linear path along a central region, pivot the X-ray source and the X-ray detector in a counterclockwise direction between the central region and a first edge of the table, and pivot the X-ray source and the X-ray detector in a clockwise direction between the central region and a second edge of the table.

A first example of the X-ray imaging device, further includes where the central region overlaps with a central axis of the patient.

A second example of the X-ray imaging device, optionally including the first example, further comprising wherein the instructions further enable the controller to perform a plurality of total body scans, the plurality of total body scans comprises transverse sweeps along the linear path and pivots at periphery regions between the first and second edges of the table and the central region.

A third example of the X-ray imaging device, optionally including one or more of the previous examples, further includes where the transverse sweeps and the pivots alternate with one another in a single, continuous motion.

A fourth example of the X-ray imaging device, optionally including one or more of the previous examples, further includes where the X-ray source produces a fan-beam, wherein the fan-beam is configured to pass through the patient before the table.

A fifth example of the X-ray imaging device, optionally including one or more of the previous examples, further includes where the X-ray detector is closer to the table than the X-ray source.

An embodiment of a system, comprises a table comprising a first side facing an X-ray source and a second side facing an X-ray detector, wherein the X-ray source is configured to move along a linear track between a first linear track edge and a second linear track edge, and wherein the X-ray source is configured to pivot counterclockwise along a first peripheral region arranged between the first linear track edge to a first edge of the table and pivot clockwise in a second peripheral region arranged between the second linear track edge to a second edge of the table.

A first example of the system further includes where the X-ray detector moves in lock-step with the X-ray source.

A second example of the system, optionally including the first example, further includes where the X-ray source is configured to execute linear sweeps along the linear track separately from pivot sweeps along the first and second peripheral regions during a first scan type.

A third example of the system, optionally including one or more of the previous examples, further includes where the X-ray source is configured to alternate linear and pivot sweeps along the linear track and the first and second peripheral regions during a second scan type.

A fourth example of the system, optionally including one or more of the previous examples, further includes where the X-ray source is a dual energy X-ray source configured to sweep in a raster pattern, wherein a patient is arranged on the first side of the table, and wherein a distance between the X-ray source and the table is greater than a distance between the table and the X-ray detector.

A fifth example of the system, optionally including one or more of the previous examples, further includes where the X-ray source is configured to execute a total scan sweep in a continuous motion.

A sixth example of the system, optionally including one or more of the previous examples, further includes where the X-ray detector is configured to pivot counterclockwise along a first peripheral region arranged between the first linear track edge to a first edge of the table and pivot clockwise in a second peripheral region arranged between the second linear track edge to a second edge of the table.

As used herein, an element or step recited in the singular and proceeded with the word "a" or "an" should be understood as not excluding plural of said elements or steps, unless such exclusion is explicitly stated. Furthermore, references to "one embodiment" of the invention do not exclude the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

The control methods and routines disclosed herein may be stored as executable instructions in non-transitory memory and may be carried out by the control system including the controller in combination with the various sensors, actuators, and other hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the control system, where the described actions are carried out by executing the instructions in a system including the various hardware components in combination with the electronic controller.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. An X-ray system, comprising:
   an X-ray source facing a pad arranged on a first side of a table, the X-ray source configured to produce a fan-beam; and
   an X-ray detector facing a second side of the table, the second side opposite the first side, wherein an object is positioned on the pad on the first side of the table and wherein the X-ray detector faces the second side of the table through an entirety of its range of movement, wherein the X-ray source is a dual-energy X-ray source configured to scan in a raster pattern, wherein the table is positioned vertically between the X-ray source and the X-ray detector, wherein the X-ray detector includes an aperture having an opening through which the fan-beam may travel following travel through the object, and wherein the opening is shaped by two blockers.

2. The X-ray system of claim 1, wherein the X-ray source is configured to actuate linearly along a first region and pivot along a second region.

3. The X-ray system of claim 2, wherein the first region is a central region, and wherein the second region is a peripheral region arranged between edges of the central region and edges of the table.

4. The X-ray system of claim 2, wherein the X-ray detector is configured to actuate linearly along the first region and pivot along the second region to maintain a normal angle of incidence between the fan-beam of the X-ray source and the X-ray detector.

5. The X-ray system of claim 2, wherein the X-ray detector is configured to travel along an arc-shaped travel path, and wherein the arc-shaped travel path maintains a fixed contact source-to-image distance.

6. The X-ray system of claim 2, wherein the X-ray detector is configured to travel along a straight line path parallel to the second side of the table.

7. The X-ray system of claim 2, wherein the X-ray detector is configured to actuate linearly along the first region, wherein the X-ray detector is configured to pivot along the second region adjacent to an edge of the table, and wherein the X-ray detector is configured to move in lock step with the X-ray source.

8. The X-ray system of claim 1, wherein the pad comprises a material that is more compressible than a material of the table.

9. The X-ray system of claim 1, wherein radiation from the X-ray source penetrates the object, then the pad, and then the table, before reaching the X-ray detector.

10. The X-ray system of claim 1, wherein the two blockers include a first blocker and a second blocker, wherein the first blocker has a first density and the second blocker has a second density, and wherein the second density is higher than the first density.

11. The X-ray system of claim 10, wherein the first blocker is configured to decrease scanner scatter.

12. The X-ray system of claim 10, wherein the first blocker includes a brass plate.

13. The X-ray system of claim 10, wherein the second blocker includes tungsten (W).

14. The X-ray system of claim 10, wherein the second blocker is configured to reduce a shadowed area in closest proximity to the X-ray detector.

15. The X-ray system of claim 1, wherein the two blockers include a first blocker and a second blocker, wherein the first blocker includes a narrowing throat from an incoming X-ray beam face toward the second blocker and the X-ray detector, wherein the narrowing throat has an aperture throat angle that is determined based on a table width and twice a source to image distance (SID), and further wherein the first blocker includes a bevel that is based on the determined aperture throat angle.

16. The X-ray system of claim 1, wherein the two blockers include a first blocker and a second blocker, and wherein the first blocker is positioned substantially above the second blocker.

17. An X-ray imaging device, comprising:
a table comprising a first side on which a patient may be positioned and a second side, opposite the first side, facing away from the patient;
a pad arranged between the first side of the table and the patient;
an X-ray source positioned closer to the first side than the second side and an X-ray detector positioned closer to the second side than the first side and facing the second side through an entirety of its range of movement, wherein the X-ray source is configured to produce a fan-beam, wherein the table is positioned vertically between the X-ray source and the X-ray detector, wherein the X-ray detector includes an aperture having an opening through which the fan-beam may travel following travel through the object, wherein the opening is shaped by two blockers, and wherein the X-ray source and the X-ray detector are configured to follow linear paths parallel to the table and pivot at peripheral regions corresponding to edges of the table; and
a controller with computer-readable instructions stored on non-transitory memory thereof that when executed enable the controller to:
actuate the X-ray source and X-ray detector along a linear path along a central region;
pivot the X-ray source and the X-ray detector in a counterclockwise direction between the central region and a first edge of the table; and
pivot the X-ray source and the X-ray detector in a clockwise direction between the central region and a second edge of the table.

18. The X-ray imaging device of claim 17, wherein the central region overlaps with a central axis of the patient.

19. The X-ray imaging device of claim 17, wherein the instructions further enable the controller to perform a plurality of total body scans, and wherein the plurality of total body scans comprises transverse sweeps along the linear path and pivots at periphery regions between the first and second edges of the table and the central region.

20. The X-ray imaging device of claim 19, wherein the transverse sweeps and the pivots alternate with one another in a single, continuous motion.

21. The X-ray imaging device of claim 17, wherein the X-ray detector is closer to the table than the X-ray source.

22. The X-ray imaging device of claim 17, wherein the pad comprises a material that is more compressible than a material of the table.

23. A system, comprising:
a table comprising a first side facing an X-ray source and a second side facing an X-ray detector, wherein the X-ray source is configured to produce a fan-beam, wherein the table is positioned vertically between the X-ray source and the X-ray detector, wherein the X-ray detector includes an aperture having an opening through which the fan-beam may travel following travel through the object, wherein the opening is shaped by two blockers, wherein the X-ray source is configured to move along a linear track between a first linear track edge and a second linear track edge, and wherein the X-ray source is actuated in a continuous motion from a first peripheral region, to a central region, and to a second peripheral region to perform a plurality of transverse sweeps along the linear track without performing a pivot.

24. The system of claim 23, wherein the X-ray detector moves in lock-step with the X-ray source.

25. The system of claim 23, wherein the X-ray source is a dual energy X-ray source configured to sweep in a raster pattern, wherein a patient is arranged on the first side of the table, and wherein a distance between the X-ray source and the table is greater than a distance between the table and the X-ray detector.

26. The system of claim 23, wherein the X-ray detector is configured to pivot counterclockwise along a first peripheral region arranged between the first linear track edge to a first edge of the table and pivot clockwise in a second peripheral region arranged between the second linear track edge to a second edge of the table.

* * * * *